United States Patent

Bettman et al.

[11] Patent Number: 5,709,886
[45] Date of Patent: Jan. 20, 1998

[54] EFFERVESCENT MICROCAPSULES

[75] Inventors: Marie Jean Bettman, Dayton; Phillip J. Percel, Troy; Thomas C. Powell, Alexandria, all of Ohio

[73] Assignee: Eurand America, Incorporated, Vandalia, Ohio

[21] Appl. No.: 802,147

[22] Filed: Feb. 19, 1997

Related U.S. Application Data

[62] Division of Ser. No. 383,342, Feb. 3, 1995, Pat. No. 5,639,475.

[51] Int. Cl.$^6$ .................................................. B01J 13/08
[52] U.S. Cl. .................. 424/495; 427/213.3; 428/402.24
[58] Field of Search ........................... 424/495, 489, 424/490, 494, 466; 427/213.3; 428/402.24

[56] References Cited

U.S. PATENT DOCUMENTS

| | | | |
|---|---|---|---|
| 1,356,544 | 10/1920 | Miller | 424/451 |
| 3,860,733 | 1/1975 | Morse et al. | 426/302 |
| 3,872,227 | 3/1975 | Hoff et al. | 514/198 |
| 4,411,933 | 10/1983 | Samejima et al. | 427/213.3 |
| 4,831,058 | 5/1989 | Pankhania et al. | 514/570 |
| 5,084,278 | 1/1992 | Mehta | 424/441 |
| 5,178,878 | 1/1993 | Wehling et al. | 424/466 |
| 5,215,755 | 6/1993 | Roche et al. | 424/480 |
| 5,306,506 | 4/1994 | Zema et al. | 424/466 |

FOREIGN PATENT DOCUMENTS

0069097-A2  1/1983  European Pat. Off. .

*Primary Examiner*—Robert H. Harrison
*Attorney, Agent, or Firm*—John W. Routh

[57] ABSTRACT

Taste masked effervescent microcapsules are provided each microcapsule containing an effervescent admixture of sodium bicarbonate and citric acid microencapsulated with ethylcellulose, the effervescent microcapsules being useful in formulating taste masked effervescent chewable tablets also containing microencapsulated, unpleasant tasting drugs such as non-steroidal, anti-inflammatory, NSAID drugs.

1 Claim, No Drawings

EFFERVESCENT MICROCAPSULES

This application is a divisional application of application Ser. No. 08/383,342, filed Feb. 3, 1995, now U.S. Pat. No. 5,639,475.

BRIEF DESCRIPTION OF THE INVENTION

The present invention is directed to taste-masked effervescent microcapsules and chewable tablets made there from. More particularly the present invention is directed to individual taste masked microcapsules each containing an effervescent admixture of sodium bicarbonate and citric acid and taste masked chewable tablets containing the effervescent microcapsules together with microcapsules containing an NSAID or other unpleasant tasting pharmaceutical material. The effervescent microcapsules of the present invention are manufactured by microencapsulating a granulation of sodium bicarbonate and citric acid in a heated coacervation medium including cyclohexane, an encapsulating polymer and a phase inducing polymer and subsequently cooling the coacervation medium. The microcapsule containing the unpleasant tasting component of the taste masked chewable tablets and the tablets themselves are manufactured by methods well known to the art.

BACKGROUND OF THE INVENTION

The process for the preparation of individual taste masked bitter tasting pharmaceuticals by microencapsulation of the pharmaceutical in a coacervation medium containing cyclohexane, an encapsulating polymer and a phase inducing agent is well known in the art. A typical process is described in U.S. Pat. No. 3,860,733 to Lewis D. Morse et al which discloses microencapsulation of vitamin mixes by polymer/polymer incompatibility coacervation. A disclosed coating polymer is ethylcellulose, a disclosed phase inducing polymer is polyethylene and a disclosed solvent for the polymers is cyclohexane. Because of its detailed description of the coacervation process, U.S. Pat. No. 3,860,733 is incorporated herein by reference in its entirely. Another description of the preparation of ethylcellulose microcapsules by the liquid-liquid phase separation of ethylcellulose in cyclohexane is given in U.S. Pat. No. 4,411,933, which patent disclosure is also incorporated herein by reference in its entirety.

Effervescent granulations and tablets made therefrom are also known to the art. For example, U.S. Pat. No. 3,872,227 to Dieter Hoff et al discloses granulations of sodium citrate, citric acid, saccharin and coloring, granulated in alcohol and dried, the granulations being a pre-mix further admixed with other materials including ampicillin and sodium bicarbonate and then tableted to form effervescent tablets.

Non-steroidal anti-inflammatory drugs (NSAID) having analgesic and anti-inflammatory properties have been widely administered orally in the treatment of mild to severe pain, particularly for rheumatoid arthritis and osteoarthritis patients. Tolerance or addiction to these drugs is not generally a problem with their continuous use in the treatment of pain or in the treatment of acute or chronic inflammatory states. However, these drugs generally have a higher potential for adverse side effects at the upper concentrations (limits) of their effective dose ranges. Therefore, it is important that such non-steroidal anti-inflammatory drugs be accurately measured and administered orally.

These non-steroidal anti-inflammatory drugs, e.g., ibuprofen and naproxen, have been widely prescribed by physicians. These drugs are in general tolerated well by most patients and provide an effective means for control of pain and inflammatory processes, particularly for the rheumatoid arthritis and osteoarthritis patients. However, these non-steroidal anti-inflammatory drugs have severe bitter taste and aftertaste, and have an adverse mouth feel when taken orally.

Therefore, in order to make wider use of them while substantially eliminating the bitter taste, aftertaste and adverse mouth feel and make these drugs more pleasant upon taking them orally, there has long been desired a way to insure delivery of these drugs in their desired concentrations while avoiding their extremely bitter taste, lingering aftertaste and adverse mouth feel effects referred to above connected with their ingestion orally thereby encouraging patient compliance.

SUMMARY OF THE INVENTION

According to this invention, taste-masked effervescent microcapsules are provided each containing an effervescent admixture of sodium bicarbonate and citric acid. The effervescent microcapsules in turn provide taste-masked effervescent chewable tablets when combined with microcapsules containing an unpleasant tasting pharmaceutical material. The taste-masked effervescent chewable tablets represent an improved delivery system for the objectionable tasting NSAIDS. For example, the taste masked effervescent microcapsules maintain a controlled effervescent reaction in the mouth without a "burst" effect. Also the effervescent microcapsules provide increased product stability and less need for humidity control during processing, for example, manufacture on a conventional tablet press.

DETAILED DESCRIPTION OF THE INVENTION

In the process of the invention, the preferred weak acid for use in providing effervescence is citric acid although other weak acids may be used such as fumaric acid and tartaric acid. The effervescence ingredients can be combined with excipients other than maltodextrin such as mannitol, sodium-citrate, dextrin and the like. The proportions of sodium bicarbonate to citric acid to excipient are about 55:40:5 in the granule product from the granulation process which can be any of the granulation processes known to the art. See for example, U.S. Pat. No. 5,084,278 although the fluid bed granulation process is preferred. The ethylcellulose concentration in the cyclohexane can vary so as to provide a suitable film coating on the granules but usually is such as to provide 2.01% to about 5.01% by weight at the encapsulated granule.

Suitable water-insoluble NSAID drug materials which can be used in accordance with this invention include, but are not necessarily limited to, the following: naproxen, ibuprofen, sulindac, diclofenac, fenclofenac, alclofenac, ibufenac, isoxepac, furofenac, tiopinac, zidometacin, acemetacin, fentiazac, clidanac, oxipinac, zomepirac sodium and pharmaceutically acceptable water-insoluble salts thereof. Other unpleasant tasting pharmaceuticals include acetaminophen and aspirin and caffeine.

The encapsulation process used to encapsulate the unpleasant tasting drug materials can be any taste masking encapsulation process known to the art, and the encapsulating polymer can be any pharmaceutically acceptable polymer such as ethycellulose, gelatin, cellulose acetate phthalate and mixtures thereof. The phase inducing substance can be sodium sulfate, sodium hexametaphosphate, polyethylene or an organosilicon polymer. Note U.S. Pat. No. 4,411,933.

The proportion of microencapsulated effervescent granules in the final taste masked tablets of the invention is generally about 8% to about 10% by weight encapsulated effervescent granules based on the weight of the taste masked tablet. The amount can be varied depending on the particular NSAID drug used in the tablet and on the degree of mouth cleansing effect desired from the effervescent material.

The ethylcellulose suitable for use as the encapsulating polymer can be any of the commercial NF types customarily used for encapsulating purposes. A typical ethylcellulose has a 45 or 50 per cent ethoxyl content and a 95–110 cps viscosity at 25° C. The amount of ethylcellulose employed can vary but for taste masking purposes, the ethylcellulose should comprise about 2.01% to 5.01% by weight of the coated granules. The ethylcellulose used in the following examples was Ethylcellulose, NF manufactured by Dow Chemical Company having a 49.4% ethoxyl content and a 103 cps viscosity at 25° C.

The polyethylene suitable for use as the phase inducer can have a molecular weight of between 5,000 and 10,000 and can be any of the commercial types customarily used for encapsulating purposes. The polyethylene used in the following examples was Epolene C-10 manufactured by Eastman Kodak Company having a viscosity at 150° C. of 8175 and a softening point of 101.6° C.

The process of the invention is now described below with reference to the specific examples.

EXAMPLE 1

This example illustrates the use of the coacervation process of the invention to provide taste masked effervescent microcapsules of sodium bicarbonate and citric acid for incorporation into taste masked NSAID containing tablets.

The granules containing the effervescent materials were prepared by granulating in a Versa Glatt top spray fluid bed unit. The charge to be granulated was composed of the following:

| Citric Acid | 40% by weight | 600 grams |
|---|---|---|
| Sodium Bicarbonate | 55% by weight | 825 grams |
| Maltodextrin (40% Solids) | 5% by weight | 75 grams |
| Water (Deionized) | | 112 grams |

The solids were introduced into the fluid bed unit and admixed at which time the water was introduced from the top sprayer to form the granulation. The inlet air temperature was about 65° C., the outlet air temperature was about 29° C. and the granulation time was 20 minutes. The granules were dried and were passed thought a 12 mesh U.S. Standard Sieve.

The microencapsulation of the effervescent granules was accomplished using the ingredients as follows:

| Cyclohexane | 2000 grams |
|---|---|
| Ethylcellulose, NF | 8 grams |
| Polyethylene C-10, NF | 40 grams |
| Granules | 400 grams |

Into a four liter glass beaker equipped with a 4 inch turbine and a switch blade baffle were placed the 2000 grams of cyclohexane, i.e. approximately 2600 milliters by volume. The dry ingredients were added to the cyclohexane media with continued agitation. The cyclohexane mixture was heated to 80° C. with 300 rpm of turbine agitation. Heat was removed when the cyclohexane mixture temperature reached 80° C. The mixture was allowed to cool slowly to 30° C. with continued agitation. At 30° C. the contents of the breaker were washed twice with fresh cyclohexane and decanted into a Buchner filter, then and tray dried overnight. The effervescent microcapsules were sieved through 12 mesh, U.S. Standard sieve, bottled and labeled.

In the above microencapsulation system, the phase ratio was 50 parts by weight of granules per part by weight of ethylcellulose, the ethylcellulose concentration was 0.4% by weight based on the weight of cyclohexane and the polyethylene concentration was 2.0% based on the weight of cyclohexane.

EXAMPLE 2

This example illustrates the use of taste masked effervescent microcapsules of Example 1 as a component of a tablet together with taste masked microcapsules containing ibuprofen as the NSAID pharmaceutical material.

The taste masked microcapsules containing ibuprofen were produced by the conventional coacervation process as follows:

Into a four liter glass beaker equipped with a stirrer were placed the below described materials:

| Material | Amount |
|---|---|
| Deionized Water | 1200 grams |
| Gelatin Solution, 10% | 600 grams |
| Sodium Hexametaphosphate Solution, 5% | 120 grams |

The above materials were heated to 48° C. and 300 grams of ibuprofen granules were added with quick stirring. The pH of the mixture was adjusted to 4.75, the mixture was slow cooled to 28° C. then fast cooled to 15° C. To the cooled mixture were added 30 milliliters of a 25% solution of glutaraldehyde and stirred overnight. The microcapsules were allowed to settle, the manufacturing medium was decanted, and the microcapsules were washed with water and dried.

The following formulation was used to manufacture 1000 tablets each having an ibuprofen content of 200 milligram. The effervescent microcapsules employed were the product of Example 1.

| Ingredients | Grams | Percent by Weight |
|---|---|---|
| Ibuprofen microcapsules | 249.0 | 34.95% |
| Mannitol USP Granular | 200.0 | 28.07% |
| Mannitol USP Powder | 175.0 | 24.56% |
| Aspartame | 8.0 | 1.12% |
| Peppermint Flavor | 6.0 | 0.84% |
| Magnesium Stearate | 3.0 | 0.42% |
| Effervescent Microcapsules | 70.0 | 9.82% |
| Colloidal Silica | 1.5 | 0.21% |
| | 712.5 | 100.00% |

The above ingredients excepting the magnesium stearate were introduced into a laboratory size V-blender and blended for 30 minutes. A small portion was removed and placed in a plastic container with the magnesium stearate and pre-blended then re-introduced into the V-blender. The entire contents were then blended for 10 minutes. The blended tablet ingredients were fed into a laboratory size tablet punch press to provide one-half inch diameter round flat tablets weighing approximately 712.5 milligrams per tablet.

The average thickness of the tablets was 0.186 inch and the average weight of 10 tablets was 712.5 milligrams per tablet. The average ibuprofen content of the tablets was 200 milligrams per tablet.

EXAMPLE 3

This example illustrates the use of taste marked effervescent microcapsules of Example 1 as a component of a tablet together with taste masked microcapsules containing naproxen as the NSAID pharmaceutical material.

The taste masked microcapsules containing naproxen were produced by the conventional coacervation process as follows:

A stainless steel encapsulation task equipped with a stirrer was used to prepare microcapsules from the below described materials:

| Material | Amount |
|---|---|
| Cellulose Acetate Phthalate, 5% Solution NF | 4000 grams |
| U.S.P. Purified Water | 4000 grams |
| Naproxen, USP (sieved + 30 mesh) | 1500 grams |
| Sodium Sulfate, USP | 1200 grams |
| U.S.P. Purified Water | 4800 grams |
| Citric Acid, USP | 267 grams |
| U.S.P. Purified Water | 1068 grams |

The first three ingredients were introduced into the task with stirring at 150 rpm. Into a separate vessel were placed the sodium sulfate and 4800 grams of water to make 6000 grams of a 20% aqueous sodium sulfate solution and the sodium sulfate solution was added dropwise and allowed to equilibrate. In a separate vessel were placed the citric acid and the 1068 grams of purified water to make 1335 grams of a 4% citric acid solution. The citric acid solution was added to the tank in sufficient amount to adjust the pH to 4.0. Agitation was stopped and the microcapsules were allowed to settle after which the supernatant liquid was decanted, the microcapsules were washed with acidulate & water, filtered onto a Buchner funnel, washed again, tray dried overnight and oven dried at 45° C. for four hours. The microcapsules were then sieved through a 30 mesh U.S. sieve.

The following formulation was used to manufacture 1000 tablets each having a naproxen content of 125 milligrams. The effervescent microcapsules employed were the product of Example 1.

| Ingredients | Grams | Percent by Weight |
|---|---|---|
| Naproxen Microcapsules | 142.0 | 21.26 |
| Mannitol USP Granules | 200.0 | 29.94 |
| Mannitol USP Powder | 200.0 | 29.94 |
| Aspartame | 8.0 | 1.20 |
| Cherry Flavor | 2.5 | 0.37 |
| Magnesium Stearate | 2.5 | 0.37 |
| Citric Acid | 2.0 | 0.299 |
| Colloidal Silica | 1.0 | 0.15 |
| Effervescent Microcapsules | 60.0 | 8.98 |
| Microcrystalline Cellulose | 50.0 | 7.48 |
| | 668.0 | 100.00 |

The above ingredients excepting the magnesium stearate were introduced into a laboratory size V-blender and blended for 30 minutes. A small portion was removed and placed in a plastic container with the magnesium stearate and pre-blended then re-introduced into the V-blender. The entire contents were then blended for 10 minutes. The blended tablet ingredients were fed into a laboratory size tablet punch press to provide one-half inch diameter round flat tablets weighing approximately 668 milligrams per tablet.

The average thickness of the tablets was 0.176 inch and the average weight of 10 tablets was 668 milligrams per tablet. The average naproxen content of the tablets was 125 milligrams per tablet.

EXAMPLE 4

This example illustrates the use of taste masked effervescent microcapsules of Example 1 as a component of a tablet together with taste masked microcapsules containing acetaminophen as the pharmaceutical material.

The taste masked microcapsules containing acetaminophen were produced by the conventional coacervation process as follows:

An encapsulation tank equipped with a stirrer was used to prepare microcapsules from the below described materials:

| Material | Amount |
|---|---|
| Cyclohexane | 425 gallons |
| Ethylcellulose, NF | 62 pounds |
| Acetaminophen, USP | 830 pounds |

Into the encapsulation tank were placed the above ingredients and the batch was heated to 80° C. with stirring at 57 rpm mixing speed. The mixture was then slow cooled to 20° C. at which point the microcapsules were allowed to settle out. The manufacturing medium was then decanted off and the microcapsules were washed, filtered and dried.

The following formulation was used to manufacture 1000 tablets each having an acetaminophen content of 160 milligrams. The effervescent microcapsules employed were the product of Example 1.

| Ingredients | Grams | Percent by Weight |
|---|---|---|
| Acetaminophen Microcapsules | 173.0 | 24.65 |
| Mannitol USP Granules | 265.0 | 37.76 |
| Mannitol USP Powder | 90.0 | 12.83 |
| Microcrystalline Cellulose | 80.0 | 11.40 |
| Grape Flavor | 3.0 | 0.43 |
| Magnesium Stearate | 3.5 | 0.50 |
| Effervescent Microcapsules | 65.0 | 9.26 |
| Citric Acid | 3.0 | 0.43 |
| Colloidal Silica | 1.0 | 0.14 |
| Blue Coloring | 0.25 | 0.04 |
| Red Coloring | 10.0 | 1.43 |
| Aspartame | 8.0 | 1.14 |
| | 701.75 | 100.00 |

The above ingredients excepting the magnesium stearate were introduced into a laboratory size V-blender and blended for 30 minutes. A small portion was removed and placed in a plastic container with the magnesium stearate and preblended before being reintroduced into the V-blender. The entire contents were then blended for 10 minutes. The blended tablet ingredients were fed into a laboratory size tablet punch press to provide one-half inch diameter round flat tablets weighing approximately 702 milligrams per tablet.

The average thickness of the tablets was 0.179 inch and the average weight of ten tablets was 702 milligrams per tablet. The average acetaminophen content of the tablets was 160 milligrams per tablet.

We claim:

1. A process for microencapsulating a finely divided admixture of sodium bicarbonate and citric acid to produce a taste masked effervescent material comprising individual microcapsules each containing an effervescent mixture of sodium bicarbonate and citric acid encapsulated with ethylcellulose, which process comprises forming a granulate admixture of sodium bicarbonate and citric acid, and charging the admixture of sodium bicarbonate and citric acid to a coascervating medium including cyclohexane as the solvent, ethylcellulose as the encapsulating polymer, and a phase inducing polymer, and separating the microcapsules.

* * * * *